(12) United States Patent
Waeschle (10) Patent No.: US 8,273,103 B2
(45) Date of Patent: Sep. 25, 2012

(54) SURGICAL NEEDLE AND METHOD OF MANUFACTURING A SURGICAL NEEDLE

(75) Inventor: Tobias Waeschle, Koenigsheim (DE)

(73) Assignee: Aesculap AG, Tuttlingen (DE)

( * ) Notice: Subject to any disclaimer, the term of this patent is extended or adjusted under 35 U.S.C. 154(b) by 796 days.

(21) Appl. No.: 11/900,396

(22) Filed: Sep. 10, 2007

(65) Prior Publication Data
US 2008/0065155 A1    Mar. 13, 2008

(30) Foreign Application Priority Data

Sep. 13, 2006 (DE) .......................... 10 2006 044 788
Sep. 18, 2006 (DE) ..................... 20 2006 014 897 U (51) Int. Cl.
*A61B 17/06* (2006.01)
(52) U.S. Cl. ........................................ 606/223; 606/222
(58) Field of Classification Search .......... 606/222–227, 606/148; 206/365, 380; 604/264, 272–274
See application file for complete search history.

(56) References Cited

U.S. PATENT DOCUMENTS

| | | | | |
|---|---|---|---|---|
| 2,728,343 A | * | 12/1955 | Everett | 606/226 |
| 3,160,157 A | * | 12/1964 | Chisman | 606/223 |
| 4,799,484 A | | 1/1989 | Smith et al. | |
| 4,932,961 A | | 6/1990 | Wong et al. | |
| 5,478,327 A | | 12/1995 | McGregor et al. | |
| 5,527,322 A | * | 6/1996 | Klein et al. | 606/144 |
| 5,649,961 A | | 7/1997 | McGregor et al. | |
| 5,665,078 A | | 9/1997 | McGregor et al. | |
| 5,853,423 A | | 12/1998 | McGregor et al. | |
| 5,913,875 A | | 6/1999 | Smith et al. | |
| 6,214,030 B1 | * | 4/2001 | Matsutani et al. | 606/223 |
| 6,322,581 B1 | * | 11/2001 | Fukuda et al. | 606/223 |
| 6,419,092 B1 | | 7/2002 | Brown | |
| 2006/0047309 A1 | | 3/2006 | Cichocki, Jr. | |

FOREIGN PATENT DOCUMENTS

| | | |
|---|---|---|
| DE | 198 04 246 | 8/1999 |
| DE | 694 22 771 | 6/2000 |
| DE | 102 59 642 | 7/2004 |
| DE | 698 21 067 | 7/2004 |
| EP | 0 286 438 | 10/1988 |
| EP | 0 648 474 | 4/1995 |
| EP | 0 809 968 | 12/1997 |
| EP | 0 898 939 | 3/1999 |

OTHER PUBLICATIONS

"Suturing material: Needle Specification", [online], [retrieved on Nov. 6, 2007], (2 pages) last updated on Mar. 1, 2005, Retrieved from the Fumedica website using Internet <URL:http://www.fumedica.de/med_in/medcoro_2_eng.html >.

"Suturing material: Needle Specification", [online], [retrieved on Nov. 6, 2007], (2 pages) last updated on Apr. 19, 2002, Retrieved from Internet Archive Wayback Machine using Internet <URL:http://web.archive.org/web/20040915011030/http://www.fumedica.de/med_in/medcoro_2_eng.html>.

* cited by examiner

*Primary Examiner* — Corrine M McDermott
*Assistant Examiner* — Gregory Anderson
(74) *Attorney, Agent, or Firm* — Lipsitz & McAllister, LLC (57) ABSTRACT

A surgical needle having an elongate needle body and a needle point formed on a distal end of the needle body, the needle body manufactured from an elongate cylindrical blank. The needle body has at least one textured-profile lateral face, which has at least one textured-profile lateral-face region provided with a textured profile, wherein the textured profile has a plurality of indentations and wherein the at least one textured-profile lateral-face region extends as far as the needle point.

20 Claims, 5 Drawing Sheets

SURGICAL NEEDLE AND METHOD OF MANUFACTURING A SURGICAL NEEDLE

The present disclosure relates to the subject matter disclosed in German patent application number 10 2006 044 788.3 of Sep. 13, 2006 and German utility model application number 20 2006 014 897.3 of Sep. 18, 2006 which are incorporated herewith by reference and in their entirety.

BACKGROUND OF THE INVENTION

The present invention relates to a surgical needle comprising an elongate needle body and a needle point formed on a distal end of the needle body, wherein the needle body is manufactured in particular from an elongate cylindrical blank.

The present invention further relates to a method of manufacturing a surgical needle comprising an elongate needle body and a needle point formed on a distal end of the needle body, wherein the needle body is manufactured in particular from an elongate cylindrical blank.

Surgical needles of the initially described type are used for example in the form of micro-needles during heart surgery. It is known to manufacture micro-needles of this type from an elongate cylindrical blank, wherein the blank is shaped by being pressed from four directions into an elongate square needle body. Such a micro-needle has a substantially square cross section and rounded longitudinal edges as well as approximately a diameter of ca. 0.2 mm. Because of their dimensions the stability of such micro-needles is limited. Furthermore, the sliding behaviour of the needle as it pierces body and tissue is limited.

Therefore, it would be desirable to provide a surgical needle, in particular a micro-needle, and a method of manufacturing a surgical needle having an improved handling ability of the surgical needle.

SUMMARY OF THE INVENTION

In a surgical needle of the initially described type, it is suggested that the needle body has at least one textured-profile lateral face, which comprises at least one textured-profile lateral-face region provided with a textured profile, wherein the textured profile comprises a plurality of indentations and wherein the at least one textured-profile lateral-face region extends as far as the needle point.

The needle proposed according to the invention, in particular in the form of a micro-needle, has the advantage that by forming the textured-profile lateral-face region the stability of the needle is markedly increased. This applies, on the one hand, to a bending strength of the needle and, on the other hand, to the sliding behaviour of the needle as it pierces tissue. Compared to known surgical needles, the sliding behaviour is improved in particular also because the textured-profile lateral-face region extends as far as the needle point, i.e. right up to the distal end of the needle point. Thus, as soon as the needle point penetrates into tissue a markedly improved sliding behaviour is achieved. What is more, the surgical needle according to the invention has a modified point design because the textured-profile lateral-face region extends right up to the end of the point, this moreover lending the needle a unique appearance. A further result of the at least one textured-profile lateral face is an improved seat in a needle holder, which is conventionally used to hold the surgical needle during surgery. Particularly in the case of surgical micro-needles, the textured profile is preferably designed in the form of a micro-profile, namely with dimensions of the indentations that are preferably smaller or even markedly smaller than a diameter of the needle body. The indentations may in particular be arranged geometrically and the textured profile may have a high degree of symmetry, for example a three-, four-, five- or six-fold symmetry.

It is advantageous if the at least one textured-profile lateral-face region forms at least half of the at least one textured-profile lateral face. Said region preferably extends over the entire textured-profile lateral face. The larger the textured-profile lateral-face region, the better the sliding behaviour of the needle body as it penetrates into tissue.

The sliding behaviour may be further improved if the needle body has two textured-profile lateral faces and if the two textured-profile lateral faces face in opposite directions away from one another. Such a needle body is moreover easy to manufacture, for example by pressing between two machine tools in the form of shaping dies that are oriented towards one another.

The needle body in cross section advantageously has a rectangular or square or substantially rectangular or square shape. Such a shape is easy to manufacture, for example by pressing from four sides.

It is advantageous if the needle body has four flat or substantially flat lateral faces and if at least one of the lateral faces is a textured-profile lateral face. That means that one, two, three or four textured-profile lateral faces may be provided in this case. Flat lateral faces may in particular be manufactured in a simple manner by pressing.

It would in principle be conceivable for all of the lateral faces of the needle body to be designed in the form of textured-profile lateral faces. It is however advantageous if the needle body has at least one non-profiled lateral face adjoining the at least one textured-profile lateral face. Such a non-profiled lateral face is much easier to manufacture than a textured-profile lateral face.

Whilst it would in principle be conceivable for the non-profiled lateral faces to be of a flat design, it is advantageous if the at least one non-profiled lateral face has a convex curvature in a direction away from the needle body. The formation of such a non-profiled lateral face, depending on the blank used, requires no further step in the method of manufacturing the needle. Preferably, two non-profiled or substantially non-profiled lateral faces are provided. Thus, manufacture of the needle may be markedly simplified.

The construction of the needle may be further simplified if the two non-profiled or substantially non-profiled lateral faces face in opposite directions away from one another.

Both the construction and the manufacture of the needle become particularly simple if the needle body has two textured-profile lateral faces and if two non-profiled or substantially non-profiled lateral faces are provided, which connect the textured-profile lateral faces to one another.

Whilst it would in principle be conceivable for the surgical needles to be of a rectilinear, i.e. non-curved design, it is advantageous if the needle body is bent. This improves in particular the handling ability during microsurgery.

It would in principle be conceivable to provide the textured-profile lateral face with a raised textured profile. According to a preferred embodiment of the invention, it may however be provided that the at least one textured-profile lateral surface defines an outer surface and that the plurality of indentations extend from the outer surface into the needle body. This means that the textured profile may be designed in the form of an embossed profile. Such a textured profile may be manufactured for example by means of dies that have raised textured profiles.

In order to increase the stability of the needle point, it is advantageous if a depth of the indentations relative to the outer surface of the at least one textured-profile lateral face decreases from a proximal end of the at least one textured-profile lateral-face region in the direction of the needle point. Thus, despite an improved sliding behaviour of both the needle point and the entire needle, the stability of the needle, in particular the bending strength thereof, may be increased despite formation of the textured profile.

In an advantageous manner, the plurality of indentations are entirely or partially of a pyramidal design. In particular, the pyramidal indentations may be designed in such a way as to produce a textured profile that corresponds, or is at least similar to an external texture of a golf ball.

Manufacture of the needle is simplified if the plurality of indentations are entirely or partially designed in the shape of square pyramids. It would of course also be conceivable to design hollow spherical indentations, in particular in the form of hollow hemispheres. It may further be provided that edges in the transition region of the indentations to the outer surface of the textured-profile lateral face are rounded off.

The surgical needle is particularly easy to manufacture if the plurality of indentations are impressed.

It is advantageous if the needle body is manufactured by injection moulding. This allows the needle to be manufactured from a wide range of materials. According to a preferred embodiment of the invention, it may be provided that the needle body is manufactured by metal injection moulding (MIM), powder injection moulding (PIM) or by plastic injection moulding. By means of the described types of manufacture, the needle body may be manufactured without having to be pressed. The needle body may therefore in particular be produced in one manufacturing operation. In particular, it is not absolutely necessary to manufacture the needle from an elongate cylindrical blank, with the result that this feature is an optional feature. Preferably, the needle is manufactured from a metal, a ceramic material or from plastics material. It would also be conceivable to use combinations of the described materials to manufacture the needle.

Conventional needle points are manufactured preferably by mechanical methods, for example by grinding the distal end of the needle body into a point. In order however to retain the textured profile right up to the distal end of the point to be formed, it is advantageous if the needle point is manufactured by electrochemical polishing. Electrochemical polishing involves a removal of material, but material is also removed from inside the indentations so that these are likewise partially abraded or altered in shape. It is therefore possible for the textured profile formed in the needle body to be retained right up to the distal end of the point. Depending on the design of the point, the depth of the individual indentations relative to the outer surface may decrease in the direction of the distal end of the point.

During the use of surgical needles, there is always a thread disposed at the proximal end of the needle. In principle, it is conceivable for the thread to be held by clamping in a thread receiver or to be connected by adhesion to the proximal end. In order to allow any desired thread to be selected, it is advantageous if the needle at a proximal end has at least one eye. A thread may be held by clamping in a notch or blind hole. For individual selection of a thread, an eye, into which the selected thread may be threaded at any time, is particularly suitable. Eyes and blind holes are suitable preferably for macro-needles. It is however also possible to provide eyes in micro-needles, wherein in the case of micro-needles it is also advantageous to provide blind holes or notches for receiving a thread.

The eye is preferably designed in the form of a through opening in the needle body that is circular, oval or elongate-hole-like in cross section. It is therefore easy to thread threads of different cross sections through the eye.

According to a preferred embodiment of the invention, it may further be provided that the needle point and/or the entire needle body are entirely or partially coated with a silicone layer. By means of a silicone coating the sliding behaviour of the needle may be further improved. The indentations of the textured profile moreover have the advantage that they may serve, so to speak, as "silicone stores" so that the sliding behaviour does not deteriorate even after repeated piercing of tissue.

Further, in a method of the initially described type, it is suggested that the needle body is provided with at least one textured-profile lateral face, that the at least one textured-profile lateral face for forming at least one textured-profile lateral-face region is provided with a textured profile, which comprises a plurality of indentations, in such a way that the at least one textured-profile lateral-face region extends as far as the needle point.

The method proposed according to the invention makes it possible to manufacture a needle, in particular a surgical micro-needle, which compared to conventional needles exhibits markedly improved sliding behaviour and moreover has greater stability, in particular a greater bending strength.

Furthermore, the indentations, especially if they are completely separate from one another, are suitable as reservoirs for sliding agent or lubricant, for example in the form of silicone, if the entire needle body is coated with a silicone layer. It is therefore possible to retain the sliding behaviour of the needle as a whole even after it has been used to pierce through tissue several times in succession.

The at least one textured-profile lateral-face region is preferably designed in such a way that it forms at least half of the at least one textured-profile lateral face. The textured-profile lateral-face region may however alternatively be designed in such a way that it forms the entire textured-profile lateral face.

The larger the textured-profile lateral-face region is, the better the sliding behaviour and the stability of the needle.

The needle may be manufactured easily, for example by pressing, if the needle body is provided with two textured-profile lateral faces such that the two textured-profile lateral faces face in opposite directions away from one another. Such a needle moreover also has the advantage that, as it penetrates into tissue, it may divide the tissue particularly easily by means of the two textured lateral faces, along which the tissue slides.

It becomes particularly easy to manufacture the needle if the needle body is designed in such a way that in cross section it has a rectangular or square or substantially rectangular or square shape.

Shaping tools for manufacturing the needle are particularly easily configured and cost-effective if the needle body is designed in such a way that it has four flat or substantially flat lateral faces and if at least one of the lateral faces is a textured-profile lateral face.

Manufacture of the needle is further simplified if the needle body is designed in such a way that it has at least one non-profiled lateral face adjoining the at least one textured-profile lateral face.

It is advantageous if the at least one non-profiled lateral face is designed with a convex curvature in a direction away from the needle body. This makes it possible to use for manufacture of the needle body in particular an elongate cylindrical blank, the remaining lateral faces of which, after provision of the at least one textured-profile lateral face with the textured profile, no longer have to be machined.

Preferably, two non-profiled or substantially non-profiled lateral faces are formed, which may be manufactured for example in a single method step of the needle body by pressing between two dies.

The optional method step just described is particularly simplified if the two non-profiled or substantially non-profiled lateral faces are designed facing in opposite directions away from one another. The stability of the needle increases and manufacture is simplified if the needle body is designed in such a way that it has two textured-profile lateral faces and that two non-profiled or substantially non-profiled lateral faces are formed, which connect the textured-profile lateral faces to one another. This allows in particular an, in cross section, square or rectangular needle profile to be formed in a simple manner, for example by means of two forming press steps.

The needle body after the formation of the at least one textured-profile lateral-face region is preferably bent. It may in this case be bent in particular in such a way that the textured-profile lateral face after the bending step still lies in one plane or alternatively in such a way that the textured-profile lateral face is curved out of the plane it originally defined. A curvature of the needle has in particular the advantage of also allowing vessels to be easily stitched to one another.

According to a preferred variant of the method according to the invention, it may be provided that the at least one textured-profile lateral face defines an outer surface and that the plurality of indentations are formed from the outer surface into the needle body. It is therefore possible in particular for a textured profile to be formed by impressing by means of a die having a raised textured profile.

In order not to reduce the stability of the needle, it is advantageous if a depth of the indentations relative to the outer surface of the at least one textured-profile lateral face is designed to decrease from a proximal end of the at least one textured-profile lateral-face region in the direction of the needle point. Despite the indentations in the region of the distal end of the needle point being no longer as deep as indentations in the region of the non-tapered needle body, the sliding behaviour of the needle is still markedly improved by the profiling of the needle point itself. In particular, such a profiled needle point may easily be manufactured by electrochemical polishing.

The textured profile is particularly easy to produce if the plurality of indentations are entirely or partially of a pyramidal design. For example, such a textured profile may be produced by means of a pressure die that has a profile of raised pyramids. In particular, this allows the needle body to be provided with a textured profile that has the shape of a textured profile known from golf balls.

It would in principle be conceivable to form the needle by injection moulding. It is however particularly advantageous if the plurality of indentations are impressed. This allows a marked improvement of a bending strength of the needle, namely because of the strain hardening of the needle body material that is brought about by the pressing operation.

As already mentioned, it may also be advantageous if the needle body is manufactured by injection moulding. This in particular allows the needle to be manufactured in a single operation. In particular, for this purpose there is no need to provide a blank. This means that no elongate cylindrical blank is required for manufacture of the needle. Rather, the material used to manufacture the needle and/or needle body may alternatively be injected into a mould that defines the shape of the finished needle. The feature, that the needle body is manufactured from an elongate cylindrical blank, is therefore an optional feature and not central to the invention.

In a preferred variant of the method according to the invention, it may be provided that the needle body is manufactured by metal injection moulding (MIM), powder injection moulding (PIM) or by plastic injection moulding. For these methods of manufacture no elongate cylindrical blank is required for forming the needle.

Depending on the intended application and desired stability, it is advantageous if the needle is manufactured from a metal, from plastics material or in the form of a ceramic by sintering.

It would in principle admittedly be conceivable to form the needle point by grinding the needle body. However, the needle point is preferably manufactured by electrochemical polishing. In this way, particularly if the basic body has been provided with a textured profile, the textured profile may be retained right up to the distal end of the needle point because with electrochemical polishing there is a removal of material not just from an outer surface but also from surfaces of the formed indentations. Although a result of this is that a depth of the indentations relative to an outer surface decreases in the direction of the distal end of the needle point with an increasing polishing period, a textured profile is nevertheless retained.

In principle, it is possible to fix a thread by clamping or adhesion directly to a proximal end of the needle body. The needle is however preferably provided at a proximal end with at least one eye, blind hole or notch. An eye in particular allows the needle to be equipped with the optimum suture material for the desired application. Blind holes and notches for fixing the thread have in particular the advantage that they may be used even in the case of very small needles, in particular micro-needles, to fasten a thread securely to the needle.

Depending on the suture material to be used, it may be advantageous if the eye is designed in the form of a through opening in the needle body that is circular, oval or elongate-hole-like in cross section.

The needle point and/or the entire needle body are preferably entirely or partially coated with a silicone layer. The silicone layer allows the needle to slide even better through tissue.

The following description of a preferred embodiment of the invention serves in connection with the drawings to provide a more detailed explanation.

DETAILED DESCRIPTION OF THE INVENTION

There now follows a description of a preferred embodiment of a surgical needle according to the invention and of a variant of a method according to the invention of manufacturing a surgical needle.

Figure 5:
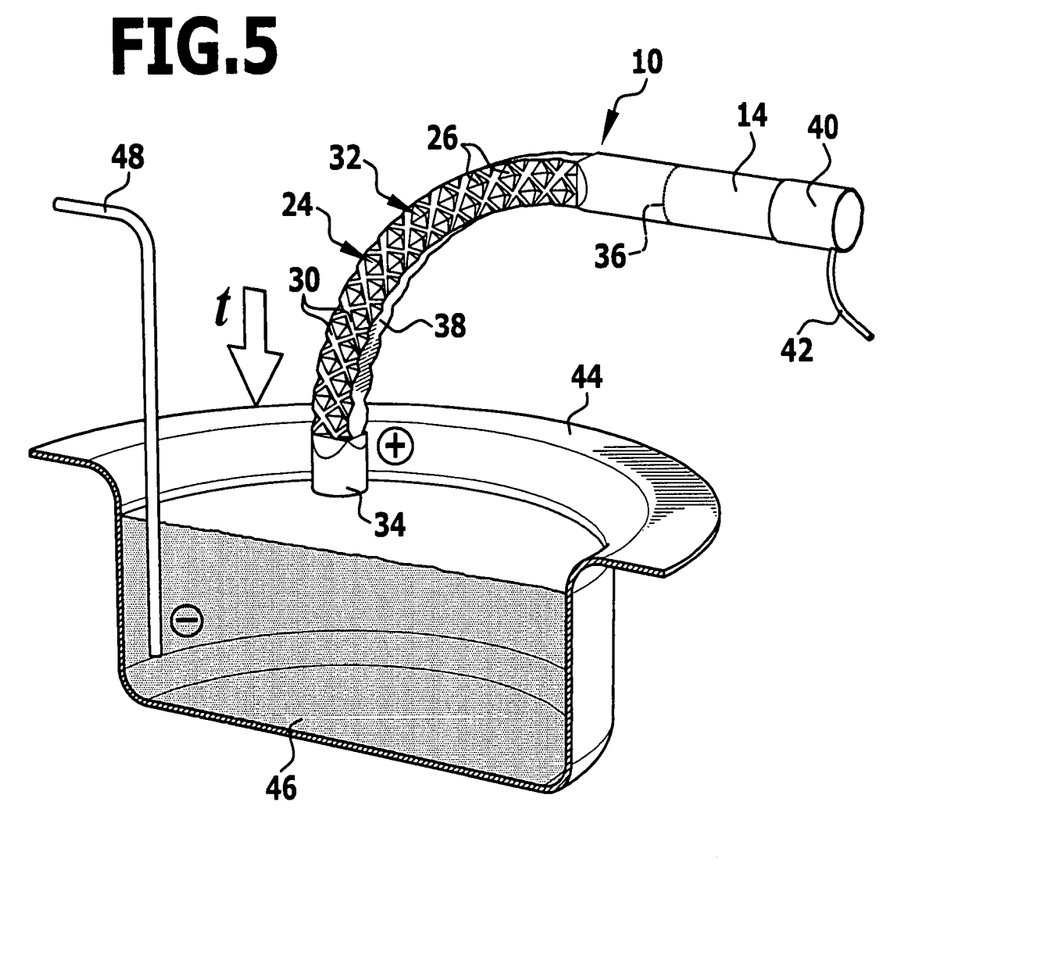
FIG. 5: a diagrammatic representation of the needle body of FIG. 4 during electrochemical polishing of the needle point.
Figure 6:
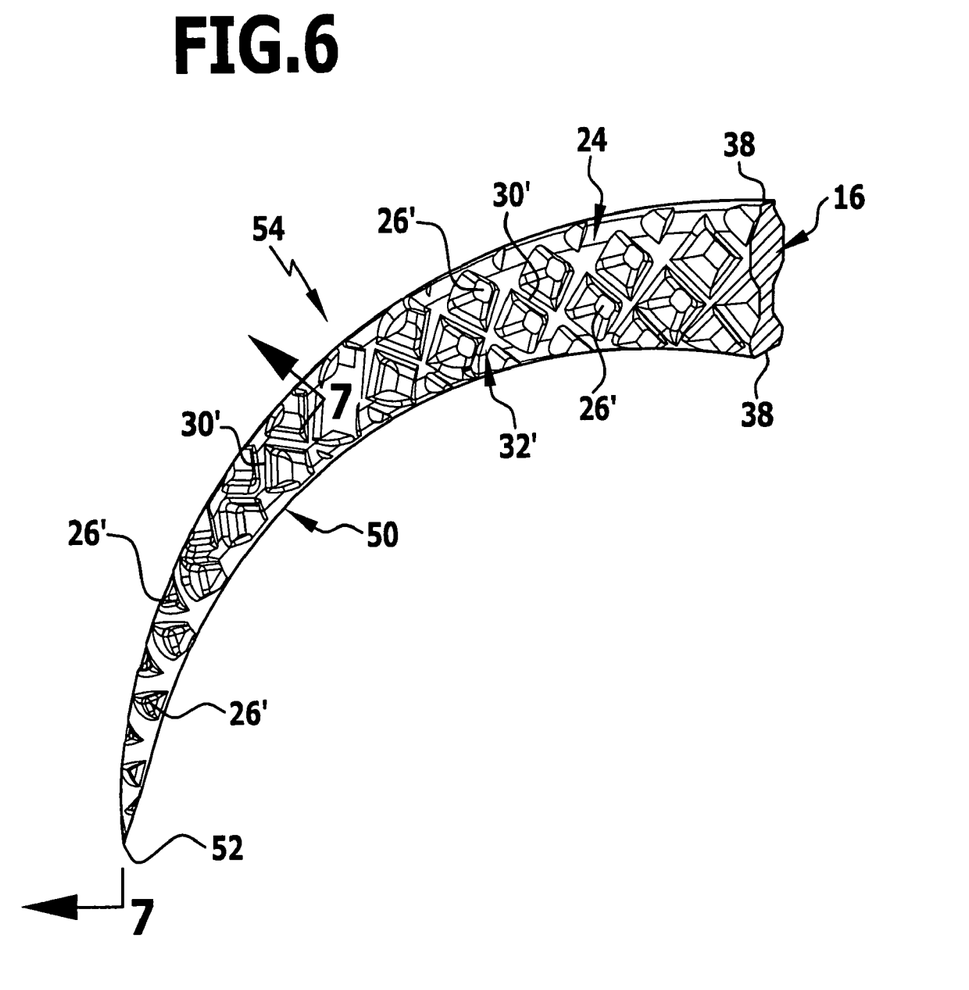
FIG. 6: a diagrammatic representation of the electrochemically polished needle point.

In the case of the embodiment of a surgical needle 54 that is described in detail with reference to FIGS. 1 to 7 and illustrated at least partially in FIGS. 6 and 7, it relates to a microsurgical needle 54 and a method of manufacturing a surgical needle 54. The starting point of the method is a blank 10 of an elongate cylindrical material, for example a metal wire, which has a circular cross section 12. Approximately one third of the length of the blank 10 serve as auxiliary shank 14, the remaining part of the blank 14 forming a basic body 16 for the surgical needle 54. Manufacture of the surgical needle is however also possible without an auxiliary shank. The blank 10 for manufacturing surgical micro- and macro-needles preferably has a diameter in a range of 0.05 mm to 1.5 mm, preferably in a range of 0.15 mm to 0.3 mm.

Figure 1:
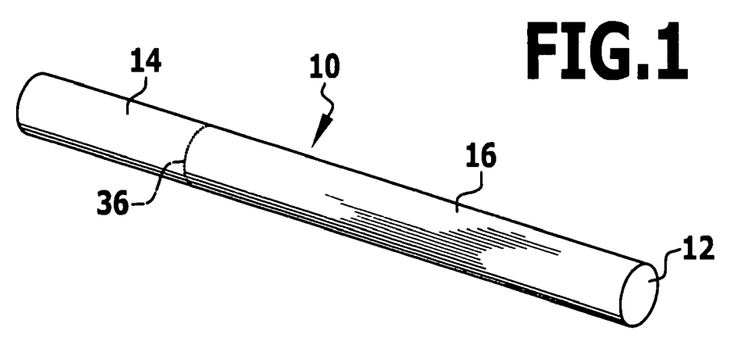
FIG. 1: a perspective view of an elongate cylindrical blank for forming a needle body.
Figure 2:
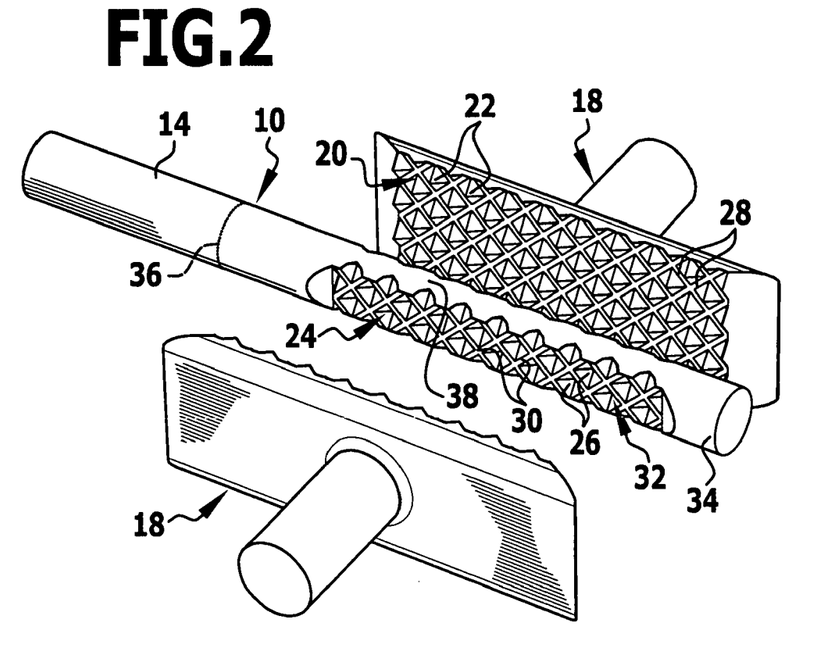
FIG. 2: a perspective representation of the blank of FIG. 1 after the impressing of two textured-profile lateral-face regions.

In a first step of manufacture of the surgical needle 54, two machine tools in the form of dies 18, which have a profiled face 20 comprising a plurality of raised square pyramids 22, are used to form two textured-profile lateral-face regions 24 on the blank, namely in that the mutually opposite profiled faces 20 of the two dies 18 are pressed against the portion of the blank 10 that forms the basic body 16 of the needle 54 until, as a result of material compression, the pyramids 22 have formed pyramid-like indentations 26 in the basic body 16. The pyramids 22 are separated by separating webs 28 that define a plane, as are the indentations 26 by separating webs 30. The separating webs 30 define an outer surface or at least part of an outer surface of a textured-profile lateral face 32 of the basic body 16. Longitudinal axes of the separating webs 30 are oriented either parallel to the longitudinal axis of the blank 10 or inclined relative to the longitudinal axis. In the embodiment represented in the figures, longitudinal axes of the separating webs are inclined by approximately 45° relative to the longitudinal axis of the blank.

By the use of two dies 18, there are formed on the basic body 16 two textured-profile lateral faces 32 facing in opposite directions away from one another.

The projections, which form the profiled face 20 and may be designed for example in the form of the described raised square pyramids 22, are preferably arranged geometrically, for example in a geometrical pattern with a multiple symmetry. In the embodiment illustrated in the Figures, the profiled face 20 has a four-fold symmetry.

Also conceivable, however, would be three- or six-fold symmetries with correspondingly shaped projections. By means of the described pressing operation the textured-profile lateral-face regions 24 are also given a corresponding symmetrical appearance.

For the formation of surgical needles, both of micro-needles and of macro-needles, use is preferably made of dies 18, the pyramids 20 of which have lateral edges with dimensions in a range of 0.02 mm to 1 mm, in particular also in a range of 0.07 mm to 0.1 mm, preferably 0.085 mm. The separating webs 28 and 30 between the pyramids 22 and the indentations 26 have a width in a range of 0.009 mm to 1 mm, in particular also in a range of 0.025 mm to 0.04 mm, preferably a width of 0.03 mm.

The textured-profile lateral-face region 24 formed by the dies 18 does not extend over the entire length of the basic body 16 but instead terminates at a slight distance from a distal end 34 of the basic body 16 as well as, at the proximal end, from a boundary region 36 between the basic body 16 and the auxiliary shank 14, which are integrally connected to one another and on completion of all of the machining steps may be separated from one another by cutting in the boundary region.

A height of the pyramids 22 relative to the plane defined by the separating webs 28 is in a range of 0.04 mm to 0.1 mm. This leads accordingly to a depth of the impressed indentations 26 relative to an outer surface defined by the separating webs 30 that is likewise in a range of 0.04 mm to 0.1 mm.

As a result of forming the textured-profile lateral-face regions 24 the basic body 16 has two textured-profile lateral faces 32 connected to one another by two non-profiled lateral faces 38, which extend in longitudinal direction of the basic body 16 and have a convex curvature in a direction away from the basic body 16. By virtue of the dies 18 each having a profiled face 20, the textured-profile lateral-face regions 24 are flat and/or substantially flat.

An optional step of the method of manufacturing the surgical needle is to bend the basic body 16. For this, there are several options. First, the basic body may be bent in such a way that a non-profiled region of the basic body 16 adjoining the boundary region 36 remains unbent, the basic body 16 being curved only in the region of the formed textured-profile lateral-face regions 24. A radius of curvature of the basic body may lie in a range of 0.5 mm to 50 mm. The distal end 34 of the basic body 16 likewise remains unbent and therefore forms a rectilinear cylindrical portion. The bending of the basic body 16 may be provided in such a way that after bending of the basic body 16 the separating webs 30 of the textured-profile lateral-face regions 24 still define two mutually parallel planes. Such a form of bending is represented for example in FIGS. 3 and 4. It would however also be conceivable for the non-profiled lateral faces 38, which because of their curvature touch two mutually parallel, not illustrated tangential planes, after bending of the basic body 16 still to define and/or touch the same two tangential planes. This possible way of bending the basic body 16 is not illustrated in the Figures.

After the optional step of bending the basic body 16, the lateral faces 38 may optionally be profiled likewise by pressing by means of two non-illustrated dies. For example, dies with flat die faces may be used so that the lateral faces 38, which initially had a concave curvature in a direction away from the basic body 16, after the pressing operation each define flat planes, which for example is easily possible with non-curved basic bodies 16 as well as with curved basic bodies, in which the lateral faces 38 after bending still touch the same two mutually parallel planes. In these cases, dies with flat stamping faces may be used.

If however, as described above and illustrated in FIGS. 3 and 4, the basic body 16 is bent in such a way that the planes formed by the separating webs 30 remain the same after bending, then for profiling and/or flattening of the lateral faces 38 of the basic body 16 two dies with curved stamping faces are used, which define, on the one hand, an inner radius of the bent basic body 16 and, on the other hand, an outer radius of the bent basic body 16.

Figure 3:
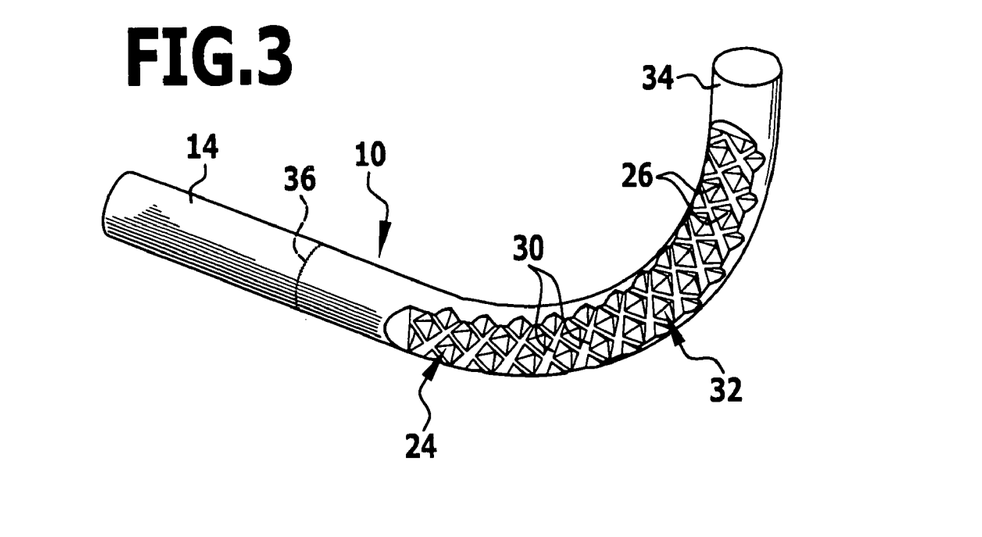
FIG. 3: the blank provided with a textured profile of FIG. 2 after bending of the basic body.
Figure 4:
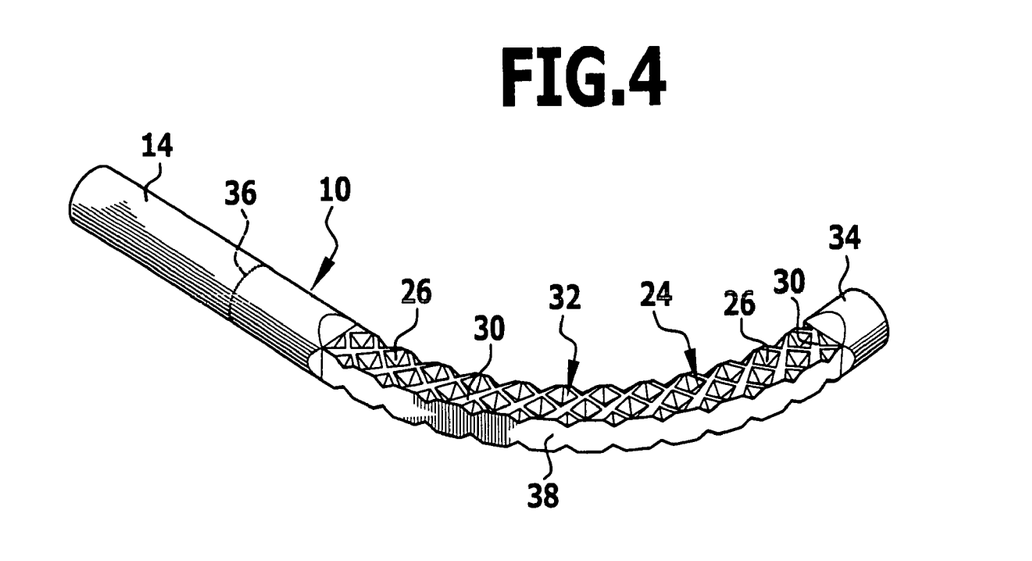
FIG. 4: a perspective view of the bent needle body of FIG. 3 after the forming of two non-profiled lateral faces.

The blank 10, which is provided with textured-profile lateral faces 24 and is optionally curved and optionally provided with profiled lateral faces 38, in the form represented in FIGS. 2 to 4 still does not have a needle point. This could admittedly be formed by machining, for example by grinding. However, this would lead to the indentations 26 being ground down until there was no longer any profile in the region of the needle point. For this reason, a needle point 50 is formed in a further processing step by electrochemical polishing. For this purpose, the auxiliary shank 14 is connected to a positive electrode, which is connected by a connection line 42 to a not-illustrated direct-voltage power supply unit. A cup-shaped container 44 filled with a suitable electrolyte 46 forms an electrolyte bath. For the electrochemical polishing operation, a negative electrode 48 that is connected for example to a negative pole of the non-illustrated power supply unit is dipped into the electrolyte 46. In order to form the needle point 50, the distal end 34 of the basic body 16 is then dipped into the electrolyte 46 and a current flow ensues. The dipping may occur successively, i.e. the basic body 16 is dipped slowly over a specific period of time into the electrolyte 46, namely to an extent corresponding to the intended length of the actual needle point 50. It would however also be conceivable to immerse the distal end 34 of the basic body 16 immediately up to the desired finished length of the needle point 50 into the electrolyte 46.

A particularly good point shape may be achieved if it ensured that the distal end 34 prior to the electrochemical polishing operation has a round cross section. The rounder the cross section at the distal end 34, the better the quality, design and stability of the needle point 50.

As a result of the electrochemical polishing, material is removed from the basic body 16, namely in the region where the basic body 16 dips into the electrolyte 46. Unlike with mechanical polishing, with electrochemical polishing material is also removed from the indentations. As a result, in the region of the needle point 50 then formed, the indentations 26 are likewise partially removed. For this reason, the needle point 50 also remains profiled up to its distal end 52, despite a depth of the indentations 26 relative to another surface defined by the separating webs 30' that separate the indentations 26' of an altered shape, is decreasing slightly in the direction of the end 52.

As a result of the electrochemical polishing operation, the originally embossed shapes of the indentations 26 moreover blend slightly together, thereby producing at the end a textured profile that is less clearly defined or might even be described as a rounded-out profile of the needle point 50.

Figure 7:
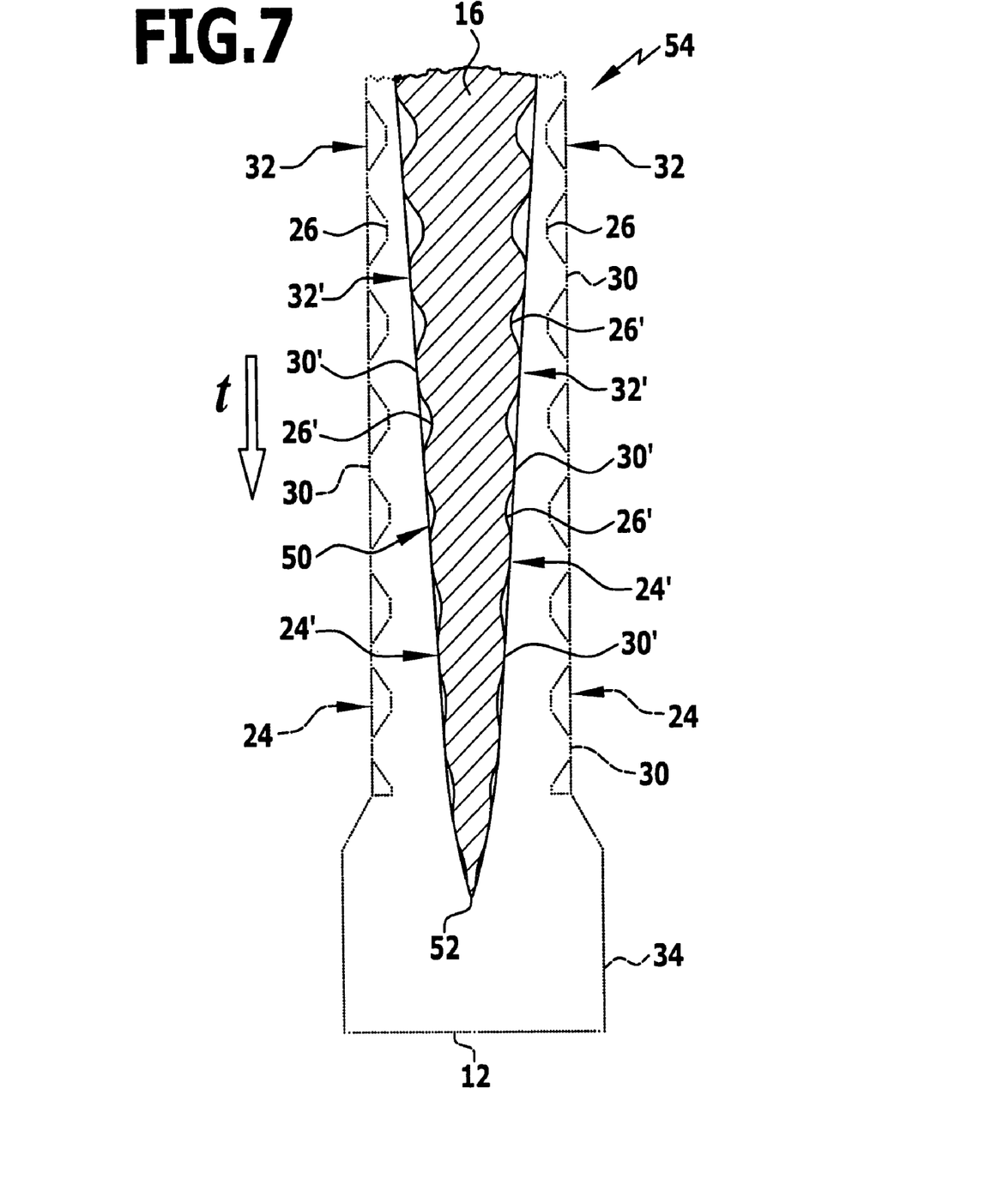
FIG. 7: a sectional view along line 7-7 through the polished needle body compared to a sectional view through the needle body prior to electrochemical polishing.

Owing to the removal of material in the region of the needle point 50, the separating webs 30 are also modified, this being indicated by way of example in FIG. 7. The indentations 26' remaining after the electrochemical polishing operation and the remaining separating webs 30' no longer correspond to the original indentations 26 and the original separating webs 30, as is apparent from the comparison of the finished needle point 50, which is shown in section, with the basic body 16 provided with textured-profile lateral-face regions 24.

The indentations 26 may also have a shape corresponding to the profiling found on golf balls, i.e. the lateral faces of the indentations 26 are curved slightly away from the basic body 16. This may be achieved for example by means of pyramids of the dies 18 that have concave lateral faces. In the plan view of such embossed indentations, they have a design in the shape of a four-pointed star that is modelled on the textured surface of a golf ball.

In a fourth but optional processing step, the needle point 50 or alternatively the entire body of the needle 54 may be siliconized, i.e. coated with a layer of silicone. As a result of forming mutually separate indentations 26, these may serve as silicone reservoirs, so that with needles manufactured in accordance with the invention tissue may be pierced several times in succession without any deterioration of the sliding behaviour of the needle body, which is improved as a result of the silicone coating.

By providing the textured profile on at least one textured-profile lateral face of the needle body the sliding behaviour of needles according to the invention is improved significantly compared to conventional needles. What is more, the bending strength is markedly improved compared to conventional needles. These marked improvements compared to the needles of prior art have the advantage that needles formed in accordance with the invention may be used to pierce tissue with less expenditure of force and the risk of the needles breaking during surgery is moreover reduced. The improvement of the bending strength of the needle is achieved in that the material, from which the blank 10 is manufactured, is strain-hardened as a result of impressing of the textured-profile lateral-face regions 24.

As already explained above, it is not absolutely necessary to form the needle according to the invention from an elongate cylindrical blank, for example from a straight, cylindrical wire nail. Rather, it is also conceivable to manufacture the needle as a whole by injection moulding, for example by metal injection moulding (MIM), powder injection moulding (PIM) or by plastic injection moulding. It would also be possible to manufacture the needle from a ceramic material by introducing the starting material into a mould and then sintering. It would optionally also be possible to manufacture a blank, as described above, by the various injection moulding techniques or by sintering and only subsequently form the point by electrochemical polishing of the needle point, in the manner described above in connection with the embodiment illustrated in the Figures.

The invention claimed is:

1. Surgical micro-needle comprising:
   an elongate needle body for a surgical micro-needle, and
   a needle point formed on a distal end of the needle body, wherein:
   the needle body is manufactured from an elongate cylindrical blank,
   the needle body has at least one textured-profile lateral face, which comprises at least one textured-profile lateral-face region provided with an embossed textured profile in a stamping process,
   the textured profile comprises a plurality of well-defined, reproducible indentations of a substantially pyramidal design,
   the needle point is formed by electrochemical polishing of the stamped needle body such that the indentations are substantially retained, and
   the at least one textured-profile lateral-face region extends as far as the needle point.

2. Needle according to claim 1, wherein the at least one textured-profile lateral-face region forms at least half of the at least one textured-profile lateral face.

3. Needle according to claim 1, wherein the needle body has two textured-profile lateral faces and the two textured-profile lateral faces face in opposite directions away from one another.

4. Needle according to claim 1, wherein the needle body in cross section has a rectangular or square or substantially rectangular or square shape.

5. Needle according to claim 1, wherein the needle body has four flat or substantially flat lateral faces and at least one of the lateral faces is a textured-profile lateral face.

6. Needle according to claim 1, wherein the needle body has at least one non-profiled lateral face adjoining the at least one textured-profile lateral face.

7. Needle according to claim 6, wherein the at least one non-profiled lateral face has a convex curvature in a direction away from the needle body.

8. Needle according to claim 6, wherein two non-profiled or substantially non-profiled lateral faces are provided.

9. Needle according to claim 8, wherein the two non-profiled or substantially non-profiled lateral faces face in opposite directions away from one another.

10. Needle according to claim 6, wherein the needle body has two textured-profile lateral faces and wherein two non-profiled or substantially non-profiled lateral faces are provided, which connect the textured-profile lateral faces to one another.

11. Needle according to claim 1, wherein the needle body is bent.

12. Needle according to claim 1, wherein the at least one textured-profile lateral face defines an outer surface and wherein the plurality of indentations extend from the outer surface into the needle body.

13. Needle according to claim 12, wherein a depth of the indentations relative to the outer surface of the at least one textured-profile lateral face decreases from a proximal end of the at least one textured-profile lateral-face region in the direction of the needle point.

14. Needle according to claim 1, wherein the plurality of indentations are entirely or partially designed in the form of square pyramids.

15. Needle according to claim 1, wherein the needle body is manufactured by injection moulding.

16. Needle according to claim 15, wherein the needle body is manufactured by metal injection moulding (MIM), powder injection moulding (PIM) or by plastic injection moulding.

17. Needle according to claim 1, wherein the needle is manufactured from a metal, a ceramic material or from plastics material.

18. Needle according to claim 1, wherein the needle at a proximal end has at least one eye, blind hole or notch.

19. Needle according to claim 18, wherein the eye is designed in the form of a through opening in the needle body that is circular, oval or elongate-hole-like in cross section.

20. Needle according to claim 1, wherein the needle point and/or the entire needle body is entirely or partially coated with a silicone layer.

* * * * *